US012508385B2

(12) United States Patent
Xu et al.

(10) Patent No.: US 12,508,385 B2
(45) Date of Patent: Dec. 30, 2025

(54) PATIENT INTERFACE DEVICE AND VENTILATION TREATMENT APPARATUS

(71) Applicant: BMC (TIANJIN) MEDICAL CO., LTD, Tianjin (CN)

(72) Inventors: Han Xu, Tianjin (CN); Yunjing Chen, Tianjin (CN); Zhi Zhuang, Beijing (CN)

(73) Assignee: BMC (TIANJIN) MEDICAL CO., LTD, Tianjin (CN)

( * ) Notice: Subject to any disclaimer, the term of this patent is extended or adjusted under 35 U.S.C. 154(b) by 889 days.

(21) Appl. No.: 17/780,511

(22) PCT Filed: Nov. 25, 2020

(86) PCT No.: PCT/CN2020/131318
§ 371 (c)(1),
(2) Date: May 26, 2022

(87) PCT Pub. No.: WO2021/104280
PCT Pub. Date: Jun. 3, 2021

(65) Prior Publication Data

US 2024/0157079 A1 May 16, 2024

(30) Foreign Application Priority Data

Nov. 27, 2019 (CN) ........................ 201911185587.7

(51) Int. Cl.
*A61M 16/06* (2006.01)
*A61M 16/08* (2006.01)
*A61M 16/10* (2006.01)

(52) U.S. Cl.
CPC .... *A61M 16/0672* (2014.02); *A61M 16/0616* (2014.02); *A61M 16/0816* (2013.01); *A61M 16/1005* (2014.02)

(58) Field of Classification Search
None
See application file for complete search history.

(56) References Cited

U.S. PATENT DOCUMENTS 3,603,313 A 9/1971 Arblaster
4,808,201 A * 2/1989 Kertzman .......... B29C 66/1122
96/10

(Continued)

FOREIGN PATENT DOCUMENTS

CN 102049080 A 5/2011
CN 203898886 U 10/2014

(Continued)

OTHER PUBLICATIONS

"JP_2019193686_translated" is the machine translated JP-2019193686 (Year: 2025).*

*Primary Examiner* — Justine R Yu
*Assistant Examiner* — Thomas Z Chang
(74) *Attorney, Agent, or Firm* — Bayramoglu Law Offices LLC

(57) ABSTRACT

The patient interface apparatus in the present application through disposing the first moisture-extraction part on the main body, it is capable to conduct the moisture in the gas cavity to outside of the main body, which may automatically remove condensed water in the gas cavity, thereby improving safety of ventilation treatment and reducing labor intensity of medical staffs.

20 Claims, 4 Drawing Sheets

(56) References Cited

U.S. PATENT DOCUMENTS

| | | | | |
|---|---|---|---|---|
| 7,493,902 | B2 * | 2/2009 | White | A61M 16/0003 128/207.18 |
| 11,058,841 | B2 * | 7/2021 | Johnson | A61M 16/0672 |
| 2004/0118401 | A1 * | 6/2004 | Smith | A61M 16/1075 128/203.26 |
| 2009/0320851 | A1 * | 12/2009 | Selvarajan | A61M 16/0683 128/207.13 |
| 2012/0285458 | A1 * | 11/2012 | Kobayashi | A61M 16/0808 128/205.12 |
| 2014/0158127 | A1 * | 6/2014 | Boucher | A61M 11/00 128/203.22 |
| 2016/0008563 | A1 | 1/2016 | Huddart et al. | |
| 2016/0030696 | A1 * | 2/2016 | Klenner | A61M 16/0066 128/207.18 |
| 2022/0184268 | A1 * | 6/2022 | Aarestad | A61L 31/10 |

FOREIGN PATENT DOCUMENTS

| | | | | |
|---|---|---|---|---|
| CN | 205434636 | U | 8/2016 | |
| CN | 109999295 | A | 7/2019 | |
| CN | 110833647 | A | 2/2020 | |
| CN | 211327569 | U | 8/2020 | |
| EP | 2522275 | A1 | 11/2012 | |
| EP | 3338847 | A2 | 6/2018 | |
| EP | 3865167 | A1 * | 8/2021 | A61M 16/0683 |
| JP | 2019193686 | A * | 11/2019 | |
| TW | 201116309 | A | 5/2011 | |

* cited by examiner

PATIENT INTERFACE DEVICE AND VENTILATION TREATMENT APPARATUS

CROSS REFERENCE TO THE RELATED APPLICATIONS

This application is the national phase entry of International Application No. PCT/CN2020/131318, filed on Nov. 25, 2020, which is based upon and claims priority to Chinese Patent Application No. 201911185587.7, filed on Nov. 27, 2019, the entire contents of which are incorporated herein by reference.

TECHNICAL FIELD

The present application relates to the field of ventilation treatment device, and particularly relates to a patient interface apparatus and a ventilation treatment device including the patient interface apparatus.

BACKGROUND

Non-invasive positive pressure ventilation has been widely used in treatment of obstructive sleep apnea (OSA), chronic obstructive pulmonary disease (COPD) and other diseases. In the non-invasive positive pressure ventilation, a blower is used to provide a continuous positive airway pressure (CPAP) or a variable pressure ventilation to a patient's airway through a tube and a patient interface apparatus, instead of surgically inserting a tube in the patient's airway.

The patient interface apparatus of the non-invasive ventilation treatment is usually provided with a nasal oxygen catheter and types of breathing masks such as a nasal mask, an oral-nasal mask and a full-face mask and so forth. Either the nasal oxygen catheter or the breathing mask, a gas cavity which is connected to the mouth/nose of the patient is provided to supply gas to the patient. During the treatment process, due to water vapor is contained in both inhaled and exhaled gas by the patient, it is very easy to condense water in the gas cavity, and excessive condensed water may pose a potential threat to the patient.

Due to the patient interface apparatus on the current market is not provided with a function of automatically removing condensed water, it requires active intervention of medical staffs, which makes the apparatus inconvenient to use and increase labor intensity of the medical staffs at the same time. Therefore, it is necessary to provide a patient interface apparatus which is capable to automatically remove condensed water, thereby improving safety of ventilation treatment and reducing labor intensity of the medical staffs.

SUMMARY

The object of the present application is to provide a patient interface apparatus and a ventilation treatment device including the patient interface apparatus, to solve the problems as mentioned above.

In order to implement the object mentioned above, one aspect of the present application provides a patient interface apparatus for a ventilation treatment device, wherein the patient interface apparatus comprises a main body and a first moisture-extraction part, wherein a gas cavity is defined inside the main body and configured to communicate with the patient's mouth and/or nose, the first moisture-extraction part is disposed on the main body and comprises a first part communicate with the gas cavity and a second part located outside the main body, the first moisture-extraction part is disposed to be capable to absorb moisture inside of the gas cavity and conduct the moisture to the second part through the first part.

Optionally, the patient interface apparatus comprises a headband, the headband is configured to fix the main body to the patient's head, the first moisture-extraction part is formed as either a part of the headband or the entire headband.

Optionally, the moisture-extraction part comprises a fixed stacked water-absorbing layer and a waterproof layer, the waterproof layer is disposed close to a side of the headband for touching the patient's head.

Optionally, the water-absorbing layer is made of fabric or absorbent dressing.

Optionally, the waterproof layer is made of plastic or rubber.

Optionally, the patient interface apparatus is a nasal oxygen catheter, the main body comprises a nasal connector and an adapting connector installed on the nasal connector, the first moisture-extraction part is installed on the nasal connector, the gas cavity is jointly limited formed by the first part, the nasal connector and the adapting connector, the adapting connector is capable to pass gas from a gas source to the gas cavity.

Optionally, the nasal connector comprises an installation structure configured to install the adapting connector, the installation structure comprises a containing cavity with a bottom opening and a top wall and a rear wall which are configured to form the containing cavity, the first part is installed on an inner surface of the rear wall, the adapting connector comprises a shell with a top opening and a rear opening, the shell is sealed and installed in the containing cavity via the bottom opening of the installation structure, the gas cavity is formed by the shell, the top wall and the first part.

Optionally, the nasal connector comprises a nasal plug configured to insert a nasal cavity, the nasal plug is disposed to extend upward along the top wall and communicate with the gas cavity.

Optionally, the nasal connector comprises two connecting walls extending outward from two ends of a left end and a right end of the rear wall, respectively, each of the connecting walls is disposed with a via hole along its extending direction, the second part of the first moisture-extraction part is disposed to extend from one end of the first part, extend and penetrate the two connecting walls and then connect to the other end of the first part.

Another aspect of the present application provides a ventilation treatment device, the ventilation treatment device comprises a host as a gas source, a ventilation tube and the patient interface apparatus as mentioned above, and the host is connected to the patient interface apparatus through the ventilation tube.

Optionally, the ventilation treatment device comprises a second moisture-extraction part, wherein the second moisture-extraction part is installed on the ventilation tube and comprises a tube inner part located in the ventilation tube and a tube outer part located outside the ventilation tube, the second moisture-extraction part is disposed to be capable to absorb moisture in the ventilation tube and conduct the moisture to the tube outer part through the tube inner part.

Optionally, a tube wall of the ventilation tube is disposed with an opening, the tube inner part is connected to the inner wall of the ventilation tube, and the tube outer part extends out of the ventilation tube through the opening in a sealed way.

Optionally, the second moisture-extraction part is a long strip shape extending along an axial direction of the ventilation tube, the tube outer part is connected to the outer wall of the ventilation tube.

Optionally, the ventilation treatment device comprises a plurality of second moisture-extraction part, the plurality of second moisture-extraction part are disposed along a circumference of the ventilation tube.

Optionally, the ventilation tube comprises a first tube and a second tube connected to one end of the first tube, one end of the first tube away from one end of the second tube is connected to the patient interface apparatus, one end of the second tube away from one end of the first tube is connected to the host, the tube inner part is connected to the inner wall of the first tube, and the tube outer part is connected to the outer wall of the second tube.

Optionally, the second tube is a heating tube.

Optionally, the second tube is inserted and connected to the first tube, the tube outer part extends to outside of the second tube through an insertion gap between the first tube and the second tube.

Optionally, the second moisture-extraction part has a tubular shape, the outer circumference of the tube inner part is connected to the inner wall of the first tube, the outer wall of the second tube is sleeved in the tube outer part.

Optionally, the second moisture-extraction part is made of fabric or absorbent dressing.

The patient interface apparatus in the present application through disposing the first moisture-extraction part on the main body, it is capable to conduct the moisture in the gas cavity to outside of the main body, which may automatically remove condensed water in the gas cavity, thereby improving safety of ventilation treatment and reducing labor intensity of medical staffs.

Other features and advantages of the present application will be described in detail in the subsequent embodiments as following.

BRIEF DESCRIPTION OF THE DRAWINGS

The attached figures are configured to provide further understanding of the present application, and being a part of the description and configured to explain the present application with the embodiments below, but do not limit the present application. In the figures.

Figure 1:
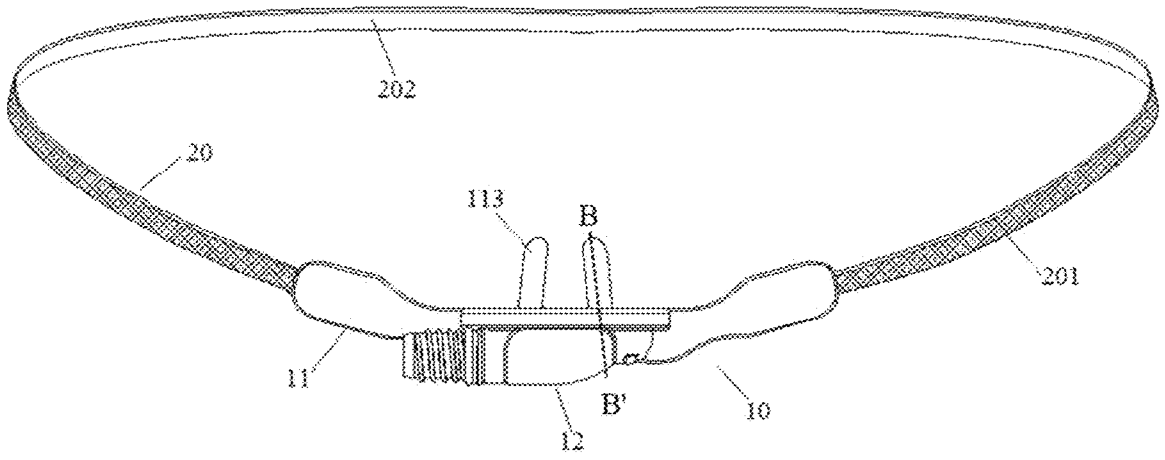
FIG. 1 is a schematic structural diagram of an embodiment of a patient interface apparatus of the present application, wherein the first moisture-extraction part forms an entire headband.

Description of labels in the attached FIGS.

10—main body, 101—gas cavity, 11—nasal connector, 111—top wall, 112—rear wall, 113—nasal plug, 114—connecting wall, 115—first flange, 116—second flange, 117—first fixing belt, 118—second fixing belt, 12—adapting connector, 121—shell, 122—top opening, 123—rear opening, 124—interface, 125—first groove, 126—second groove, 20—first moisture-extraction part, 201—water-absorbing layer, 202—waterproof layer, 21—first part, 22—second part, 30—ventilation tube, 31—first tube, 32—second tube, 40—second moisture-extraction part, 41—tube inner part, 42—tube outer part.

DETAILED DESCRIPTION OF THE EMBODIMENTS

The following is a detailed description of the embodiments of the present application in combination with the attached figures. It should be understood that the embodiments described herein are intended only to illustrate and explain the present application and are not intended to limit the present application.

In the present application, in the absence of any indication to the contrary, locational terms such as "up, down, top, bottom, left, right, rear" are generally used to refer to the orientation of the patient who is in a standing state. "Inside and outside" refers to the inside and outside of the parts relative to their own contours.

In one aspect, the present application provides a patient interface apparatus for a ventilation treatment device, wherein the patient interface apparatus includes a main body 10 and a first moisture-extraction part 20, wherein a gas cavity 101 is defined inside the main body 10 and configured to communicate with the patient's mouth and/or nose, the first moisture-extraction part 20 is installed on the main body 10, and it includes a first part 21 connected to the gas cavity 101 and a second part 22 located outside the main body 10, the first moisture-extraction part 20 is disposed to be capable to absorb moisture inside of the gas cavity 101 and conduct the moisture to the second part 22 through the first part 21.

In the mentions above, it should be noted that the first part 21 may communicate with the gas cavity 101 through various ways. For example, the first part 21 may be directly disposed inside the gas cavity 101, or it may be a part limiting the gas cavity 101. In addition, the first moisture-extraction part 20 is an integral part. Moisture in the gas cavity 101 may include water vapor in gas supplied to a patient for inhalation, water vapor in gas exhaled by the patient and condensed water generated in the gas cavity 101.

When using the product, after the first part 21 of the first moisture-extraction part 20 absorbs the moisture in the gas cavity 101, it will diffuse and conduct the moisture to the second part 22, due to the second part 22 is located at external environment of the main body 10, and the external environment humidity is low, relatively dry, so the moisture in the second part 22 is constantly evaporate to the external environment.

The patient interface apparatus of the present application is capable to export the moisture in the gas cavity 101 to the outside of the main body 10 by disposing the first moisture-extraction part 20 on the main body 10, and automatically remove the condensed water in the gas cavity 101, thus improving safety of the ventilation treatment and reducing labor intensity of medical staffs.

In the present application, the first moisture-extraction part 20 may be an additionally disposed component or may be disposed as attaching other components of the patient interface apparatus. Due to the patient interface apparatus usually includes a headband configured to fix the main body 10 to the patient's head, therefore, according to an embodiment of the present application, the first moisture-extraction part 20 may be formed as either a part of the headband or an entire headband (see FIG. 1-FIG. 3)

The headband will come into contact with the patient's head when the patient interface apparatus is placed on the patient's head. In order to improve the comfort of wearing the apparatus for the patient, the first moisture-extraction part 20 may include a fixed stacked water-absorbing layer 201 and a waterproof layer 202, and the waterproof layer 202 is disposed close to a side of the headband for touching the patient's head. It should be understood that the first moisture-extraction part 20 with the waterproof layer 202 mentioned above is more suitable for the situation where the first water-extraction part 20 touches the patient's head. In other embodiments, the first water-extraction part 20 may just include the water-absorbing layer 201.

In the present application, the waterproof layer 202 of the first moisture-extraction part 20 may be made of impermeable materials such as plastic or rubber and so forth. In order to improve the comfort of wearing, the waterproof layer 202 is preferably made of softer materials such as silica-gel and so forth. The water-absorbing layer 201 of the first moisture-extraction part 20 may be made of fabric or absorbent dressing, the water-absorbing layer 201 may be single or multi-layer structure. In addition, when the first part 21 is used to limit the gas cavity 101, the water-absorbing layer located in the first part 21 may be preferably provided with a characteristic of good water absorption but high permeability resistance, which may reduce the loss of gas for the patient to inhale and improve the sealing performance of the gas cavity 101. That is, the first part 21 and the second part 22 of the first water-extraction part 20 may be made of different materials.

In the present application, the patient interface apparatus may be a nasal oxygen catheter or a nasal mask, an oral-nasal mask, a full-face mask and so forth. The present application is further introduced by taking the nasal oxygen catheter as an example.

As referring to FIG. 1, a nasal oxygen catheter is shown, a main body 10 includes a nasal connector 11 and an adapting connector 12 installed on the nasal connector 11, a first moisture-extraction part 20 is installed on the nasal connector 11, a gas cavity 101 is jointly limited formed by the first part 21, the nasal connector 11 and the adapting connector 12, and the adapting connector 12 is capable to pass gas from a gas source into the gas cavity 101.

In the mentions above, it should be understood that the nasal connector 11 is the part configured to connect to the nasal cavity of the patient; the gas source is an apparatus that produces pressurized air or breathable gas, such as a host of a ventilation treatment device. In addition, the nasal connector 11 may be made of flexible materials (such as silica-gel), the adapting connector 12 may be made of materials harder than the nasal connector 11 (such as plastic) in order to support the nasal connector 11, so that it may ensure that the nasal connector is not easy to deform while comfortable wearing it, thereby ensuring ventilation of the nasal oxygen catheter, and improving reliability of the ventilation of the nasal oxygen catheter.

Figure 4:
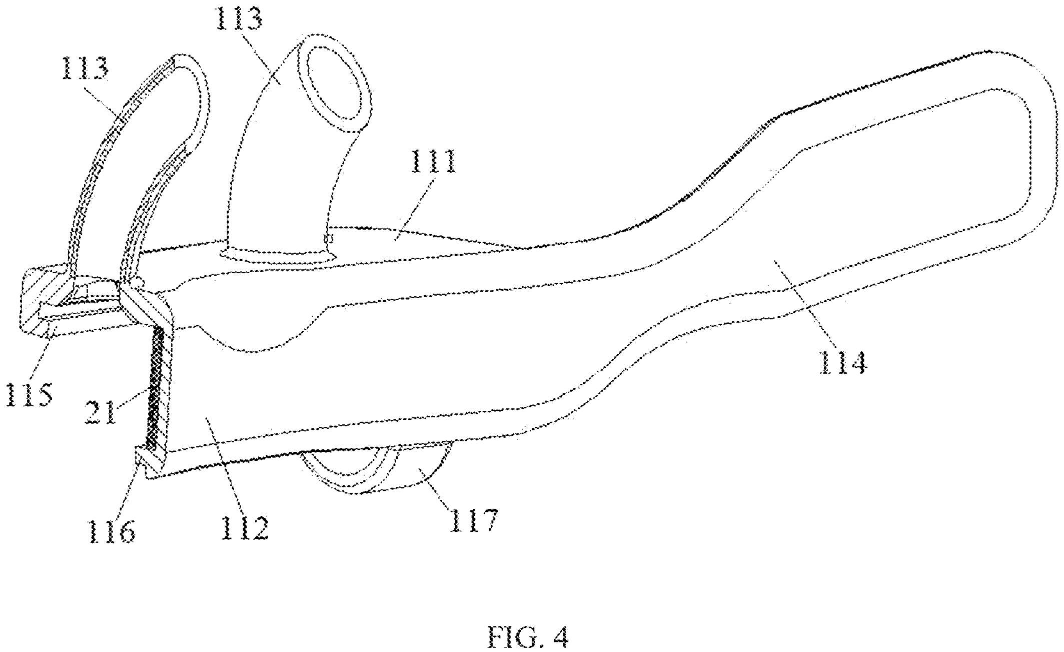
FIG. 4 is a front sectional view taken along line A-A' of FIG. 2, wherein a second part of the first moisture-extraction part is omitted.
Figure 5:
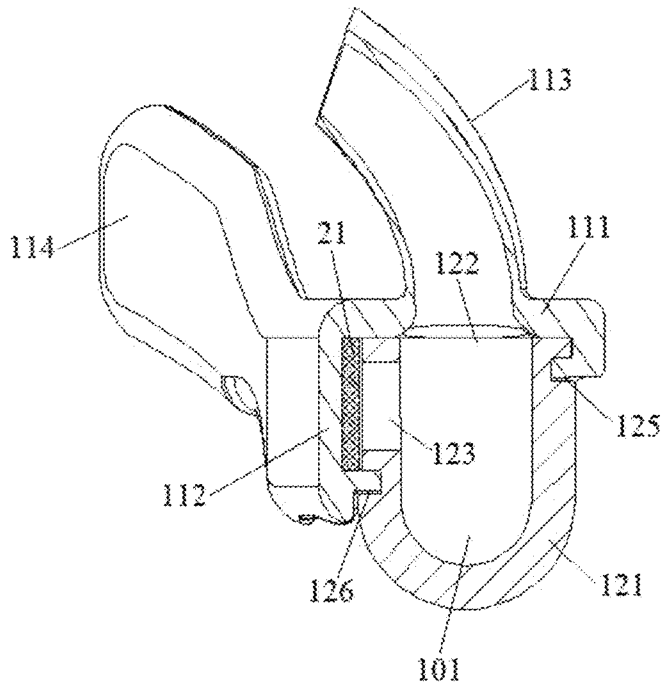
FIG. 5 is a side sectional view taken along line B-B' of FIG. 1, wherein the second part of the first moisture-extraction part is omitted.

Further, as referring to FIG. 4 and FIG. 5, the nasal connector 11 may include an installation structure configured to install the adapting connector 12. The installation structure includes a containing cavity with a bottom opening and a top wall 111 and a rear wall 112 which are configured to limit the containing cavity. The first part 21 is installed on the inner surface of the rear wall 112. The adapting connector 12 includes a shell 121 with a top opening 122 and a rear opening 123. The shell 121 is sealed and installed in the containing cavity via the bottom opening of the installation structure, and the gas cavity 101 is formed by the shell 121, the top wall 111 and the first part 21. In the mentions above, the top wall 111 seals the top opening 122 of the shell 121, the first part 21 seals the rear opening 123 of the shell 121.

In the mentions above, the shell 121 is sealed and installed in the containing cavity, which means that there is no space between the outer wall of the shell 121 and the top wall 111 and the rear wall 112 (as referring to FIG. 5). Further, the shell 121 and the top wall 111 and the rear wall 112 may be clamped through matching structures of flanges and grooves, thereby improving reliability and air tightness of the assembly. Particularly, as referring to FIG. 4 and FIG. 5, the top wall 111 is disposed with a first flange 115 which extends downward along the edge of the top wall 111, the outer wall of the shell 121 is disposed with a first groove 125 which is matched with the first flange 115; the rear wall 112 is disposed with a second flange 116 extending forward from the inner surface of the rear wall 112, the outer wall of the shell 121 is disposed with a second groove 126 which is matched with the second flange 116. In addition, as referring to FIG. 5, an installation groove is formed between the second flange 116 and the top wall 111 which is for the first part 21 embedding in.

Figure 2:
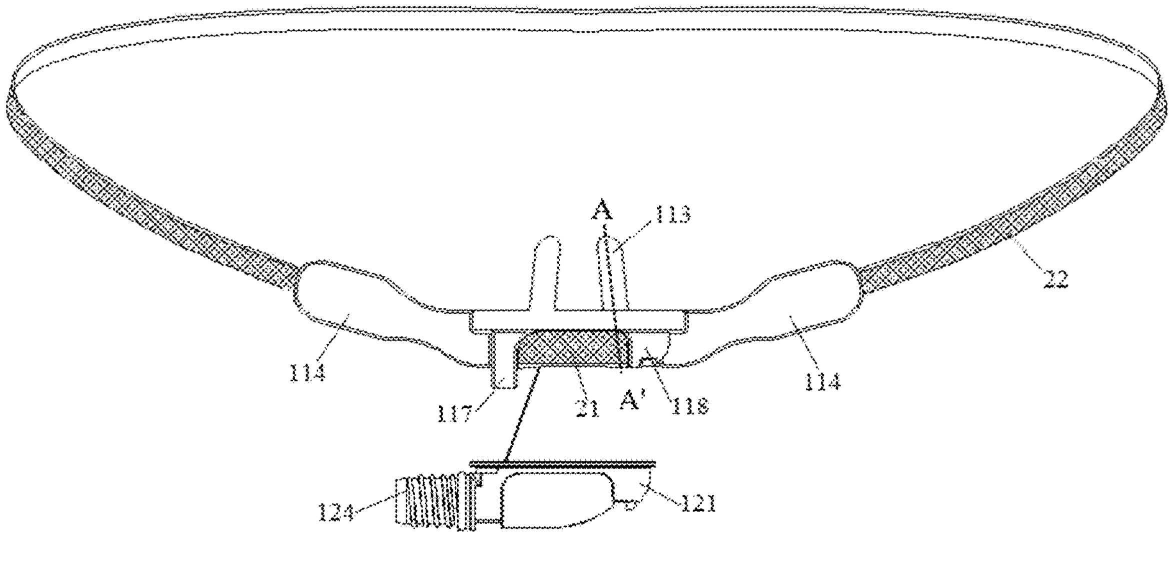
FIG. 2 is an explosive diagram of FIG. 1.
Figure 3:
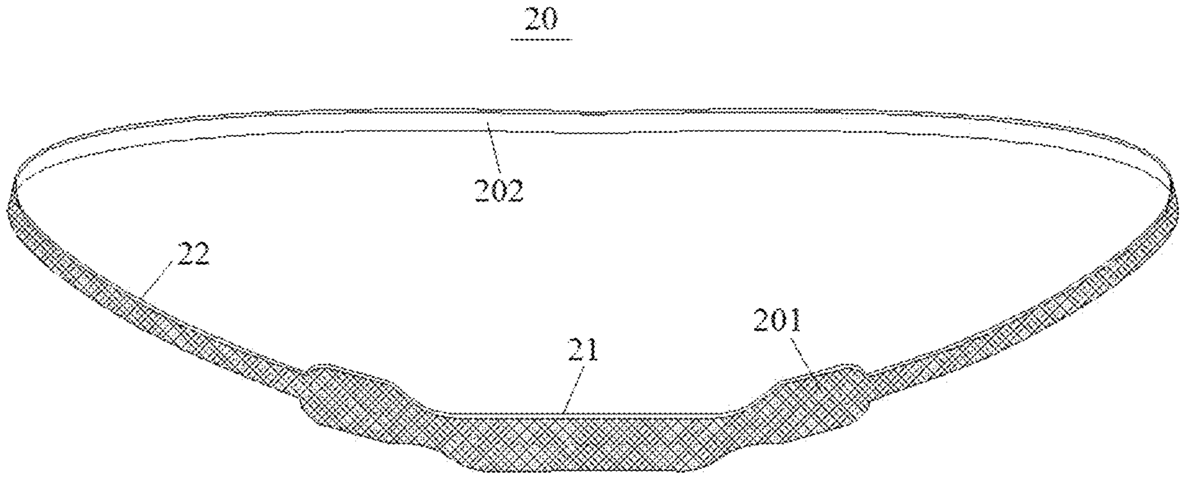
FIG. 3 is a schematic diagram of the first moisture-extraction part shown in FIG. 1.

In the present application, on the condition that the first moisture-extraction part 20 is formed as a headband, in order to strengthen the connection between the first moisture-extraction 20 and the nasal connector 11, as referring to FIG. 2, the nasal connector 11 may include two connecting walls 114 extending outward from two ends of a left end and a right end of the rear wall 112, respectively. Each of the connecting walls 114 is disposed with a via hole along its extending direction. The second part 22 of the first moisture-extraction part 20 is disposed to extend and pass through the two connecting walls 114 from one end of the first part 21 and then connect to the other end of the first part 21. It should be explained that during manufacturing, the first moisture-extraction 20 may be molded together with the nasal connector 11.

In addition, as referring to FIG. 4 and FIG. 5, the nasal connector 11 may also include a nasal plug 113 configured to insert a nasal cavity, the nasal plug 113 is disposed to extend upward along the top wall 111 and connect to the gas cavity 101. It should be understood that quantity of the nasal plug 113 is two.

In the present application, as referring to FIG. 1, the adapting connector 12 may also include an interface 124 configured to connect to a ventilation tube 30 of the gas source, the interface 124 is disposed on the shell 121 and communicate with the gas cavity 101. When using the product, the gas from the gas source passes the ventilation tube 30 and the interface 124 to enter the gas cavity 101, then enters the nasal cavity of the user through the nasal plug 113, through the top opening 122 of the shell 121.

In addition, in order to improve reliability of the assembly of the adapting connector 12 and the nasal connector 11, and to further improve air tightness of the nasal oxygen catheter, the nasal connector 11 may include a fixing part which configured to fix the adapting connector 12 to the installation structure.

The fixing part may be a fixing belt of which two ends are connected to the top wall 111 and the rear wall 112, respectively, to form a penetrating space which allows the adapting connector 12 to penetrate. Particularly, as referring to FIG. 1 and FIG. 2, the fixing belt may include a first fixing band 117 and a second fixing band 118 which are interval disposed along the penetrating direction (the direction from left to right as shown in FIG. 2) of the adapting connecter 12. The circumferential profile of the shell 121 may be disposed as decreasing gradually along its penetrating direction. Correspondingly, the penetrating space formed by the first fixing band 117 is larger than that formed by the second fixing band 118. That is, when the adapting connector 12 is installed on the nasal connector 11, the right end of the shell 121 may be easily penetrate the first fixing band 117, and then penetrate inside of the second fixing band 118. The assembly is very simple. In addition, in order to prevent gas leakage from the end being tipped up of the adapting connector 12 which matches the second fixing belt 118, the end of the second fixing band 118 which is away from the first fixing band 117 may be disposed as a closed form (as referring to FIG. 2). At this point, the adapting connector 12 may only be inserted from the left side of the first fixing band 117, but may not be inserted from the right side of the second fixing band 118.

Another aspect of the present application provides a ventilation treatment device, the ventilation treatment device includes the patient interface apparatus as mentioned above.

In the present application, the ventilation treatment device may be a ventilator, a high-flow treatment device and so forth.

The ventilation treatment device may also include a host as the gas source and a ventilation tube 30, the host may connect to the patient interface apparatus through the ventilation tube 30. Particularly, when the patient interface apparatus is a nasal oxygen catheter, one end of the ventilation tube 30 may be connected to a gas outlet of the host, the other end of the ventilation tube 30 may be connected to an interface 124 of the adapting connector 12 of the nasal oxygen catheter.

In the present application, the ventilation treatment device may also include a second moisture-extraction part 40, the second moisture-extraction part 40 is installed on the ventilation tube 30 and includes a tube inner part 41 located in the ventilation tube 30 and a tube outer part 42 located outside the ventilation tube 30, the second moisture-extraction part 40 is disposed to be capable to absorb moisture in the ventilation tube 30 and conduct the moisture to the tube outer part 42 through the tube inner part 41.

When using the product, after the tube inner part 41 of the second moisture-extraction part 40 absorbing the moisture in the ventilation tube 30, it will diffuse and conduct the moisture to the tube outer part 42, due to the tube outer part 42 located at external environment of the ventilation tube 30, and the external environment humidity is low, relatively dry, the moisture in the tube outer part 42 is constantly evaporate to the external environment.

In the present application, by installing the second moisture-extraction part 40 on the ventilation tube 30, condensate water formed in the gas cavity 101 of the patient interface apparatus may flow to the ventilation tube 30, and then be exported by the second moisture-extraction part 40.

It should be noted that the second moisture-extraction part 40 is a similar part to the first moisture-extraction part 20, but since the second moisture-extraction part 40 does not touch the head of the patient, the second moisture-extraction part 40 may only include water-absorbing layer, which may be a single or multi-layer structure made of fabric or absorbent dressing.

In some embodiments, in order to reduce the patient's discomfort caused by gas way dryness and so forth when using the product, the ventilation treatment device may also include a humidifying device configured for heating and humidifying gas, the gas after humidifying may be conveyed to the patient interface apparatus through the ventilation tube 30. Under this condition, the disposing of the second moisture-extraction part 40 may also prevent excessive condensed water formed by humidified gas in the ventilation tube 30 and get into the patient's respiratory tract and cause potentially risks.

Figure 6:
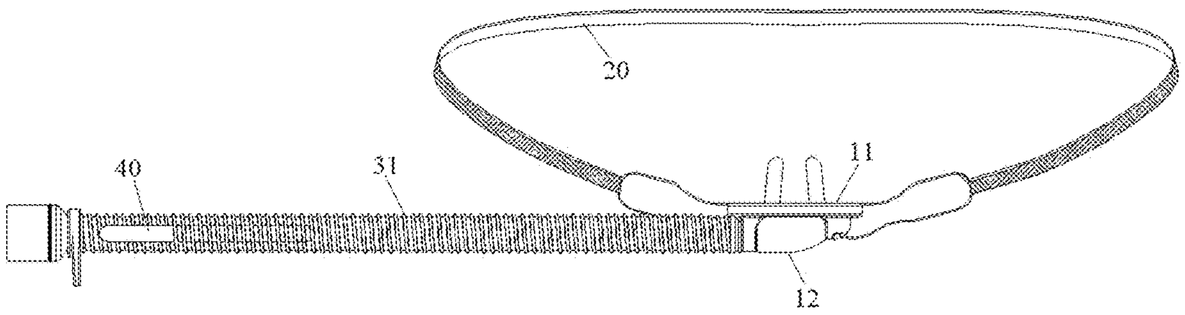
FIG. 6 is a schematic structural diagram of an embodiment of a ventilation treatment device of the present application, wherein only a patient interface apparatus and a ventilation tube are shown.

According to an embodiment of the ventilation tube 30 in the present application, as referring to FIG. 6, the ventilation tube 30 may include a first tube 31, the second moisture-extraction part 40 may be installed on the first tube 31, the tube inner part 41 of the second moisture-extraction part 40 is located inside of the first tube 31, and the tube outer part 42 of the second moisture-extraction part 40 is located outside of the first tube 31.

Figure 7:
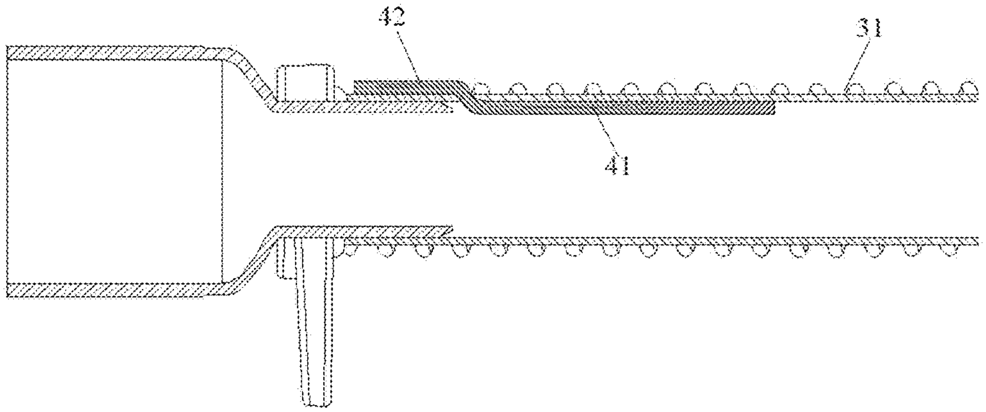
FIG. 7 is a partial sectional view of FIG. 6.

For installation of the second moisture-extraction part 40, as referring to FIG. 7, an opening may be disposed on tube wall of the first tube 31, the tube inner part 41 is connected to inner wall of the first tube 31, the tube outer part 42 is sealed by the opening and extends outside the first tube 31. The tube inner part 41 of the second moisture-extraction part 40 may be fixed to the inner wall of the first tube 31 by means of bonding or hot-melt welding, the tube outer part 42 may be connected to the outer wall of the first tube 31, or it may not be connected to the outer wall of the first tube 31. In order to improve sealing performance of the first tube 31, during manufacturing, the second moisture-extraction 40 is preferably to be molded together with the first tube 31 to from as an entirety.

In the present application, the second moisture-extraction part 40 may be provided with any shape. Particularly, the implementation way as referring to FIG. 6 and FIG. 7, the second moisture-extraction part 40 may be a long strip shape extending along the axial direction of the first tube 31, the tube outer part 42 is connected to the outer wall of the first tube 31.

Further, in order to improve extraction effect of moisture in the first tube 31, the ventilation tube 30 may include a plurality of second moisture-extraction part 40, the plurality of second moisture-extraction part 40 may be disposed along the circumference of the first tube 31.

The description above introduces the situation of that the ventilation tube 30 includes one tube (that is the first tube 31), in other embodiments of the present application, the ventilation tube 30 may be formed by connecting a plurality of tubes, under this situation, each of the tubes may be installed with the second moisture-extraction part 40, respectively, or the second moisture-extraction part 40 may be installed between two adjacent tubes.

Figure 8:
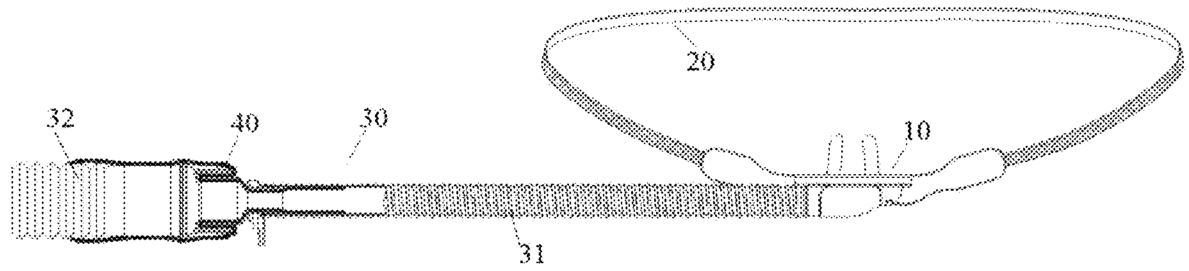
FIG. 8 is a schematic structural diagram of another embodiment of the ventilation treatment device of the present application, wherein only the patient interface apparatus and the ventilation tube are shown, the ventilation tube is shown in the sectional view and a second tube is shown incompletely.

Particularly, the embodiment as referring to FIG. 8, the ventilation tube 30 may also include a second tube 32, the second tube 32 is connected to one end of the first tube 31, the tube inner part 41 of the second moisture-extraction part 40 is connected to the inner wall of the first tube 31, and the tube outer part 42 is connected to the outer wall of the second tube 32.

Figure 9:
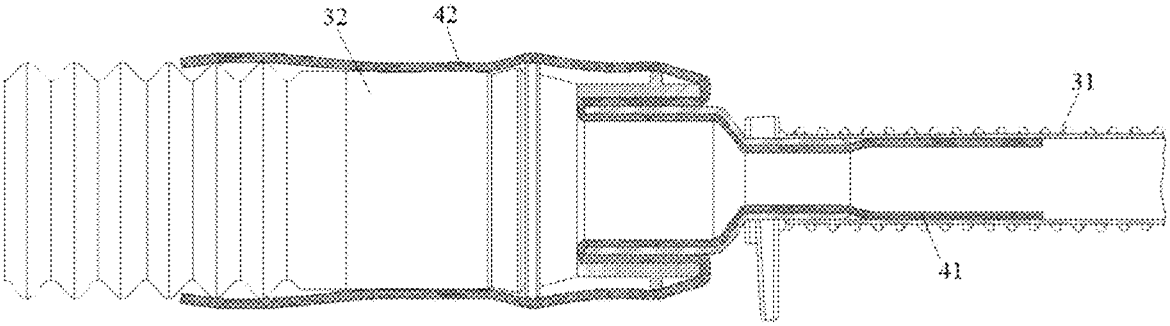
FIG. 9 is a partial enlargement view of the ventilation tube in FIG. 8.

Further, as referring to FIG. 8 and FIG. 9, the second tube 32 may be inserted to the first tube 31, the tube outer part 42 of the second moisture-extraction part 40, through an insertion space between the first tube 31 and the second tube 32, extends to outside of the second tube 32. Under this situation, the second moisture-extraction part 40 may have a tubular shape, so that the outer circumference surface of the tube inner part 41 is connected to the inner wall of the first tube 31, and the outer wall of the second tube 32 is directly sleeved in the tube outer part 42.

In the mentions above, the second tube 32 may be a heating tube. Under this situation, due to the tube outer part 42 of the second moisture-extraction part 40 touches the outer wall of the second tube 32, so that evaporation of moisture in the tube outer part 42 may be accelerated, thereby improving moisture extraction effect. When using the product, one end of the first tube 31 away from the second tube 32 may be connected to the patient interface apparatus, and one end of the second tube 32 away from the first tube 31 may be connected to the host.

The mentions above combining the attached figures to describe the optimized embodiments specifically, however, the present application is not limited to the specific details of the implementation ways above, in the scope of the technical concept of the present application, the technical solution may be changed in various simple variants, which are all belonging to the protection scope of the present application.

It should also be noted that the specific technical characteristics described in the above specific embodiments may be combined in any appropriate manner without contradiction. In order to avoid unnecessary repetition, the present application does not specify the possible combination ways separately.

In addition, the various embodiments of the present disclosure may also be arbitrarily combined, which shall be deemed to be the content disclosed by the present application, as long as they do not violate the idea of the present application.

What is claimed is:

1. A patient interface apparatus for a ventilation treatment device, wherein the patient interface apparatus comprises a main body and a first moisture-extraction part, wherein a gas cavity is defined inside the main body and configured to communicate with a mouth and/or a nose of a patient, the first moisture-extraction part is disposed on the main body, the first moisture-extraction part comprises a first part communicating with the gas cavity and a second part located outside the main body, and the first moisture-extraction part is configured to absorb moisture inside of the gas cavity and convey the moisture to the second part through the first part;

wherein the main body comprises a nasal connector and an adapting connector installed on the nasal connector;

the nasal connector comprises a fixing part which is configured to fix the adapting connector to an installation structure, the installation structure is configured to install the adapting connector, the installation structure comprises a containing cavity with a bottom opening, and a top wall and a rear wall of the installation structure are configured to form the containing cavity, and the fixing part is a fixing belt of which two ends are connected to the top wall and the rear wall;

the fixing belt comprises a first fixing band and a second fixing band which are interval disposed along a penetrating direction of the adapting connector; and a penetrating space formed by the first fixing band is larger than a penetrating space formed by the second fixing band.

2. The patient interface apparatus according to claim 1, wherein the patient interface apparatus further comprises a headband, the headband is configured to fix the main body to a head of the patient, and the headband comprises the first moisture-extraction part.

3. The patient interface apparatus according to claim 2, wherein the moisture-extraction part comprises a fixed stacked water-absorbing layer and a waterproof layer, and the waterproof layer is disposed close to a side of the headband for touching the head of the patient.

4. The patient interface apparatus according to claim 3, wherein a material of the fixed stacked water-absorbing layer is fabric or absorbent dressing, and/or a material of the waterproof layer is plastic or rubber.

5. The patient interface apparatus according to claim 1, wherein the patient interface apparatus is a nasal oxygen catheter, the first moisture-extraction part is installed on the nasal connector, the gas cavity is enclosed by the first part, the nasal connector, and the adapting connector, and the adapting connector is configured to pass gas from a gas source to the gas cavity.

6. The patient interface apparatus according to claim 1, wherein the installation structure comprises a containing cavity with a bottom opening, and a top wall and a rear wall of the installation structure are configured to form the containing cavity, the first part is installed on an inner surface of the rear wall, the adapting connector comprises a shell with a top opening and a rear opening, the shell is sealed and installed in the containing cavity via the bottom opening of the installation structure, and the gas cavity is formed by the shell, the top wall, and the first part.

7. The patient interface apparatus according to claim 6, wherein the nasal connector comprises a nasal plug configured to insert into a nasal cavity, the nasal plug is disposed to extend upward along the top wall and communicate with the gas cavity; and/or, the nasal connector comprises two connecting walls extending outward from two ends of a left end and a right end of the rear wall, respectively, each of the two connecting walls is disposed with a via hole along an extending direction of the via hole, the second part of the first moisture-extraction part is disposed to extend from a first end of the first part and penetrate the two connecting walls and then connect to a second end of the first part.

8. A ventilation treatment device, wherein the ventilation treatment device comprises a gas source, a ventilation tube, and the patient interface apparatus according to claim 1, wherein the gas source is connected to the patient interface apparatus through the ventilation tube.

9. The ventilation treatment device according to claim 8, wherein the ventilation treatment device further comprises a second moisture-extraction part, wherein the second moisture-extraction part is installed on the ventilation tube, the second moisture-extraction part comprises a tube inner part located in the ventilation tube and a tube outer part located outside the ventilation tube, and the second moisture-extraction part is configured to absorb moisture in the ventilation tube and convey the moisture to the tube outer part through the tube inner part.

10. The ventilation treatment device according to claim 9, wherein a tube wall of the ventilation tube is disposed with an opening, the tube inner part is connected to an inner wall of the ventilation tube, and the tube outer part extends out of the ventilation tube through the opening in a sealed way.

11. The ventilation treatment device according to claim 10, wherein the second moisture-extraction part has a long strip shape extending along an axial direction of the ventilation tube, and the tube outer part is connected to an outer wall of the ventilation tube.

12. The ventilation treatment device according to claim 11, wherein the ventilation treatment device comprises a plurality of the second moisture-extraction part, and the plurality of the second moisture-extraction part are disposed along a circumference of the ventilation tube.

13. The ventilation treatment device according to claim 9, wherein the ventilation tube comprises a first tube and a second tube connected to one end of the first tube, one end of the first tube away from one end of the second tube is connected to the patient interface apparatus, one end of the second tube away from one end of the first tube is connected to the gas source, the tube inner part is connected to the inner wall of the first tube, and the tube outer part is connected to the outer wall of the second tube.

14. The ventilation treatment device according to claim 13, wherein the second tube is a heating tube.

15. The ventilation treatment device according to claim 13, wherein the second tube is inserted and connected to the first tube, the tube outer part extends to outside of the second tube through an insertion gap between the first tube and the second tube; and/or the second moisture-extraction part has a tubular shape, an outer circumference surface of the tube inner part is connected to the inner wall of the first tube, and the outer wall of the second tube is sleeved in the tube outer part.

16. The ventilation treatment device according to claim 9, wherein a material of the second moisture-extraction part is fabric or absorbent dressing.

17. The ventilation treatment device according to claim 8, wherein the patient interface apparatus further comprises a headband, the headband is configured to fix the main body to a head of the patient, and the headband comprises the first moisture-extraction part.

18. The ventilation treatment device according to claim 17, wherein the moisture-extraction part comprises a fixed stacked water-absorbing layer and a waterproof layer, and the waterproof layer is disposed close to a side of the headband for touching the head of the patient.

19. The ventilation treatment device according to claim 18, wherein a material of the fixed stacked water-absorbing layer is fabric or absorbent dressing, and/or a material of the waterproof layer is plastic or rubber.

20. The ventilation treatment device according to claim 8, wherein the patient interface apparatus is a nasal oxygen catheter, the first moisture-extraction part is installed on the nasal connector, the gas cavity is enclosed by the first part, the nasal connector, and the adapting connector, and the adapting connector is configured to pass gas from a gas source to the gas cavity.

* * * * *